United States Patent [19]

Plath et al.

[11] Patent Number: 4,496,391
[45] Date of Patent: Jan. 29, 1985

[54] HERBICIDES CONTAINING 3-ARYL-5-METHYLPYRAZOLE-4-CARBOXYLIC ACID ESTERS, THEIR MANUFACTURE AND USE

[75] Inventors: Peter Plath, Ludwigshafen; Wolfgang Rohr, Wachenheim; Bruno Wuerzer, Otterstadt, all of Fed. Rep. of Germany

[73] Assignee: BASF Aktiengesellschaft, Fed. Rep. of Germany

[21] Appl. No.: 459,988

[22] Filed: Jan. 21, 1983

Related U.S. Application Data

[62] Division of Ser. No. 150,751, May 19, 1980, abandoned.

[51] Int. Cl.³ .................. A01N 43/56; A01N 43/10
[52] U.S. Cl. .................................. 71/92; 71/90
[58] Field of Search ........................ 71/92, 90

[56] References Cited

U.S. PATENT DOCUMENTS 4,116,673  9/1978  Brannigan et al. ............... 71/92

Primary Examiner—Catherine L. Mills
Attorney, Agent, or Firm—Keil & Weinkauf

[57] ABSTRACT

Herbicides containing a pyrazole derivative of the formula

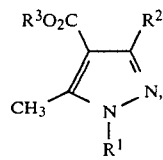

where $R^1$ denotes hydrogen, formyl, acetyl, propionyl, chloroacetyl, dichloroacetyl, methoxyacetyl, methoxycarbonyl, or phenoxycarbonyl which is unsubstituted or mono- or polysubstituted by halogen, $R^2$ denotes phenyl which is unsubstituted or mono- or polysubstituted by fluorine, chlorine, bromine, methyl, methoxy, cyano, nitro, trifluoromethyl, trifluoromethoxy or methoxycarbonyl, $R^2$ further denotes a 5- or 6-membered, heterocyclic aromatic ring which is unsubstituted or substituted by methyl or chlorine and which contains 1 or 2 hetero-atoms X, X being independently oxygen, sulfur or nitrogen, or $R^2$ denotes α-naphthyl or β-naphthyl, and $R^3$ denotes methyl, ethyl or isopropyl, or a salt of such a pyrazole derivative, a process for combating unwanted plant growth with the active ingredients and methods of manufacturing the herbicides.

1 Claim, No Drawings

HERBICIDES CONTAINING 3-ARYL-5-METHYLPYRAZOLE-4-CARBOXYLIC ACID ESTERS, THEIR MANUFACTURE AND USE

This is a division of application Ser. No. 150,751 filed May 19, 1980, now abandoned.

The present invention relates to valuable herbicides containing esters of 3-aryl-5-methylpyrazole-4-carboxylic acid.

The use of 1-ethyl-3-arylpyrazole-4-carboxylic acid esters as herbicides has been disclosed (U.S. Pat. No. 4,116,673). However, the application rate employed in the biological examples therein is 11.2 kg of active ingredient per hectare. In the general description of the utility of the compounds, preferred application rates are stated to be 5.6 kg or more of active ingredient per hectare. Particularly when the prior art compounds are used postemergence, no special herbicidal action can be expected. No crop plants are mentioned which do not react to the active ingredients.

We have now found that 3-aryl-5-methyl-4-alkoxycarbonylpyrazoles of the formula

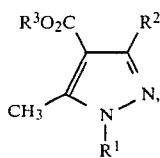

where $R^1$ denotes hydrogen, formyl, acetyl, propionyl, chloroacetyl, dichloroacetyl, methoxyacetyl, methoxycarbonyl, or phenoxycarbonyl which is unsubstituted or mono- or polysubstituted by halogen, $R^2$ denotes phenyl which is unsubstituted or mono- or polysubstituted by fluorine, chlorine, bromine, methyl, methoxy, cyano, nitro, trifluoromethyl, trifluoromethoxy or methoxycarbonyl, $R^2$ further denotes a 5- or 6-membered, heterocyclic aromatic ring which is unsubstituted or substituted by methyl or chlorine and which contains 1 or 2 heteroatoms X, X being independently oxygen, sulfur or nitrogen, or $R^2$ denotes α-naphthyl or β-naphthyl, and $R^3$ denotes methyl, ethyl or isopropyl, and salts of such pyrazole derivatives, have a surprisingly strong herbicidal action on numerous unwanted plants, especially when used postemergence, and are acceptably tolerated by various crop plants.

The pyrazole derivatives may be in the form of salts with conventional inorganic or organic acids, such hydrochloric acid, sulfuric acid, formic acid, methanesulfonic acid, trichloroacetic acid and p-toluenesulfonic acid.

The pyrazole derivatives are usually in isomer form (where $R^1$ is H, in tautomer form). Where in the following it is not specifically mentioned that only one of the two isomers is present, then the other isomer shall also be taken to be meant by a certain formula or designation without this fact having to be specifically mentioned.

In the formula of the pyrazole derivatives, $R^1$ denotes for instance hydrogen, formyl, acetyl, propionyl, chloroacetyl, dichloroacetyl, methoxyacetyl, methoxycarbonyl, phenoxycarbonyl, p-bromophenoxycarbonyl, 2,3-dichlorophenoxycarbonyl, 3,4-dichlorophenoxycarbonyl or 2,4-dichlorophenoxycarbonyl.

$R^2$ denotes for example phenyl, α-naphthyl, β-naphthyl, 2-methylphenyl, 3-methylphenyl, 2-fluorophenyl, 3-fluorophenyl, 4-fluorophenyl, 3-chlorophenyl, 4-chlorophenyl, 3-bromophenyl, 3-nitrophenyl, 3-trifluoromethylphenyl, 4-trifluoromethylphenyl, 3-methoxyphenyl, 3-(1,1,1-trifluoromethyloxy)-phenyl, 4-(1,1,1-trifluoromethyloxy)-phenyl, 3-cyanophenyl, 2,4-dichlorophenyl, 2,5-dichlorophenyl, 3,4-dichlorophenyl, 3,5-dichlorophenyl, 2,6-difluorophenyl, 3,5-dimethylphenyl, 3-methoxycarbonylphenyl, 2-methoxycarbonylphenyl, thienyl-2, thienyl-3, 4-chlorothienyl-3, furyl-2, furyl-3, 4-methyloxazolyl-5, pyridyl-2, pyridyl-3, pyridyl-4 or 2,6-dichloropyridyl-4.

$R^3$ denotes for instance methyl, ethyl or isopropyl.

The active ingredients may be manufactured for instance by any one of the following 5 processes:

(1) Reaction of 2-aroyl-3-methylaminocrotonic acid alkyl esters with hydrazine hydrate (Ber., 42, 3912, 1909).

(2) Reaction of 2-aroylacetoacetic acid esters with hydrazine hydrate (Ann., 279, 248, 1894).

(3) Oxidation of 3-aryl-4-alkoxycarbonyl-5-methylpyrazolines. First of all, for example alkyl benzalacetoacetate is reacted with hydrazine hydrate, and the pyrazoline-carboxylic acid ester which is obtained is oxidized. This method of manufacture has, however, only been disclosed for pyrazole-4-carboxylic acid ethyl esters substituted in the 2-position by phenyl, which exhibit no herbicidal action. (Ber., 59, 611, 1926).

(4) Addition of diazoethane to phenylpropiolic acid alkyl esters. One of the preferred compounds, 3-phenyl-4-methoxycarbonyl-5-methylpyrazole, was first produced by this route. (Comp. Rend., 273, Ser. C, 1772, 1971).

(5) Reaction of substituted or unsubstituted thiobenzhydrazide with 2-chloroacetoacetic acid alkyl esters (Ark. Kemi, 8, 537, 1955).

The preferred method of manufacture is the one given under 1). The manufacture is described in more detail below.

SPECIFICATION 1

Manufacture of 3-phenyl-4-methoxycarbonyl-5-methylpyrazole (a) Methyl methylaminocrotonate At 5° to 10° C., 186 g (2.4 moles) of a 40% strength aqueous methylamine solution is dripped into a solution of 232 g (2 moles) of methyl acetoacetate in 150 ml of water. The mixture is then stirred for 12 hours at room temperature (20° C.). The product is then separated from the solution by suction filtration. After washing with ice water and drying under reduced pressure, there is obtained 212 g (82%) of a white solid; m.p.: 62°–63° C.

(b) 2-Benzoyl-3-methylamino-2-butenoic acid methyl ester 193.5 g (1.5 moles) of methyl methylaminocrotonate is dissolved in 450 ml of toluene, and 166.7 g (1.65 moles) of triethylamine is added; while cooling at 0° to 5° C., 211 g (1.5 moles) (=174 ml) of benzoyl chloride is then dripped into this mixture. After the mixture has been stirred for 12 hours at 25° C., the precipitated triethylamine hydrochloride is filtered off and the toluene solution is extracted with water. After the toluene phase has been dried with $Na_2SO_4$, the residue is evaporated under reduced pressure and the solid which is obtained is recrystallized from a 4:1 mixture of ligroin and toluene. There is obtained 217 g (62%) of a white solid; m.p.: 75°–77° C.

(c) 3-Phenyl-4-methoxycarbonyl-5-methylpyrazole

At 25° to 30° C., 48.8 g (0.98 mole) of hydrazine hydrate is dripped into a solution of 217 g (0.93 mole) of the intermediate obtained under (b) in 400 ml of glacial acetic acid. The mixture is then heated for 1 hour at 100° C. After cooling to 5° C. and the addition of 600 ml of glacial acetic acid, a white solid precipitates out which is separated and washed with $NaHCO_3$-water. Drying under reduced pressure gives 182 g (91%) of the pyrazole derivative; m.p.: 119°–120° C.

The following compounds were obtained analogously:

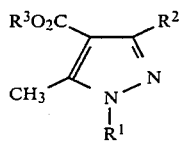

| No. | $R^1$ | $R^2$ | $R^3$ | m.p. (°C.) |
|---|---|---|---|---|
| 1 | H | phenyl | methyl | 119–120 |
| 2 | H | phenyl | ethyl | 95–96 |
| 3 | H | phenyl | isopropyl | 75–77 |
| 4 | H | α-naphthyl | methyl | 142–143 |
| 5 | H | 2-methylphenyl | methyl | 99 |
| 6 | H | 3-methylphenyl | methyl | 103–105 |
| 7 | H | 2-fluorophenyl | methyl | 95–96 |
| 8 | H | 3-fluorophenyl | methyl | 96 |
| 9 | H | 4-fluorophenyl | methyl | 110 |
| 10 | H | 3-chlorophenyl | methyl | 84–85 |
| 11 | H | 4-chlorophenyl | methyl | 116–118 |
| 12 | H | 3-bromophenyl | methyl | 63–65 |
| 13 | H | 3-nitrophenyl | methyl | 185–186 |
| 14 | H | 3-$CF_3$-phenyl | methyl | 100–103 |
| 15 | H | 4-$CF_3$-phenyl | methyl | 104–105 |
| 16 | H | 3-methoxyphenyl | methyl | 85–87 |
| 17 | H | 4-(1,1,1-trifluoromethyloxy)-phenyl | methyl | 83–84 |
| 18 | H | 3-cyanophenyl | methyl | 162–164 |
| 19 | H | 2,4-dichlorophenyl | methyl | 105 |
| 20 | H | 2,5-dichlorophenyl | methyl | 130 |
| 21 | H | 3,4-dichlorophenyl | methyl | 178–180 |
| 22 | H | 3,5-dichlorophenyl | methyl | 156–158 |
| 23 | H | 2,6-difluorophenyl | methyl | 114–117 |
| 24 | H | 3,5-dimethylphenyl | methyl | 175 |
| 25 | H | thienyl-2 | methyl | 122–124 |
| 26 | H | thienyl-3 | methyl | 135–137 |
| 27 | H | 4-chlorothienyl-3 | methyl | 93–95 |
| 28 | H | furyl-2 | methyl | 116–119 |
| 29 | H | furyl-3 | methyl | 113–115 |
| 30 | H | 4-methyloxazolyl-5 | methyl | 133–134 |

If $R^1$ is not hydrogen, the compounds may be manufactured as follows.

SPECIFICATION 2

Manufacture of 1-acetyl-3-phenyl-4-methoxycarbonyl-5-methylpyrazole 17 g (0.08 mole) of the pyrazole derivative produced in accordance with specification 1 is dissolved in 40 ml of acetic anhydride, and the solution briefly boiled. After 15 minutes, the mixture is allowed to cool before being poured on to 150 g of ice. The product has crystallized out completely after 30 minutes' stirring. The white solid is filtered off and dried under reduced pressure.

Yield: 19.6 g (95%); m.p.: 77°–78° C.

The position of the acetyl radical was inferred from spectroscopic data (nmr spectrum). It can only be definitely proved by X-ray structure analysis.

SPECIFICATION 3

Manufacture of 1-phenoxycarbonyl-3-phenyl-4-methoxycarbonyl-5-methylpyrazole 8.9 g (0.088 mole) of triethylamine is added to a solution of 17.3 g (0.08 mole) of the pyrazole derivative obtained in accordance with specification 1 in 100 ml of tetrahydrofuran; at 15° to 20° C., 12.6 g (0.084 mole) of phenyl chloroformate is then dripped in. After the mixture has been stirred for 16 hours at 25° C., the precipitated triethylamine hydrochloride is filtered off. The filtrate is evaporated under reduced pressure and the solid which remains is stirred with water. The product is then separated from the solution by suction filtration and dried under reduced pressure.

Yield: 25 g (98%); m.p.: 162°–163° C.

The following compounds were obtained analogously:

| No. | $R^1$ | $R^2$ | $R^3$ | m.p. °C. |
|---|---|---|---|---|
| 31 | acetyl | phenyl | methyl | 77–78 |
| 32 | acetyl | phenyl | ethyl | 83–86 |
| 33 | phenoxycarbonyl | phenyl | methyl | 162–163 |
| 34 | acetyl | 3-cyanophenyl | methyl | 112–115 |
| 35 | acetyl | 3-nitrophenyl | methyl | 135–137 |
| 36 | acetyl | 3-trifluoromethylphenyl | methyl | 67–68 |
| 37 | acetyl | 4-trifluoromethylphenyl | methyl | 50–53 |
| 38 | acetyl | 2-fluorophenyl | methyl | 71–74 |
| 39 | acetyl | 3-fluorophenyl | methyl | 75–78 |
| 40 | acetyl | 4-fluorophenyl | methyl | 122–123 |
| 41 | acetyl | 3-chlorophenyl | methyl | 92–94 |
| 42 | acetyl | 3-bromophenyl | methyl | 79–80 |
| 43 | acetyl | 4-chlorophenyl | methyl | 109–111 |
| 44 | acetyl | 2,5-dichlorophenyl | methyl | 80–83 |
| 45 | acetyl | 3,4-dichlorophenyl | methyl | 132–134 |
| 46 | acetyl | 3,5-dichlorophenyl | methyl | 130–133 |
| 47 | acetyl | thienyl-2 | methyl | 67–69 |
| 48 | H | 2,6-dichloropyridyl-4 | methyl | 172 |
| 49 | H | pyridyl-2 | methyl | 155–158 |
| 50 | formyl | phenyl | methyl | |
| 51 | propionyl | phenyl | methyl | |
| 52 | chloroacetyl | phenyl | methyl | 112–115 |
| 53 | dichloroacetyl | phenyl | methyl | |
| 54 | methoxyacetyl | phenyl | methyl | 115–117 |
| 55 | methoxycarbonyl | phenyl | methyl | 84–86 |
| 56 | 2-chlorophenoxycarbonyl | phenyl | methyl | 117–118 |
| 57 | 4-chlorophenoxycarbonyl | phenyl | methyl | 147 |
| 58 | 2,4-dichlorophenoxycarbonyl | phenyl | methyl | 115–117 |
| 59 | 2,5-dichlorophenoxycarbonyl | phenyl | methyl | 110–114 |

-continued

| No. | R¹ | R² | R³ | m.p. °C. |
|---|---|---|---|---|
| 60 | 3,4-dichlorophenoxycarbonyl | phenyl | methyl | 130–132 |
| 61 | 3,5-dichlorophenoxycarbonyl | phenyl | methyl | 125–128 |
| 62 | 2,3-dichlorophenoxycarbonyl | phenyl | methyl | 140–143 |
| 63 | 4-bromophenoxy- | phenyl | methyl | 154 |
| 64 | H | 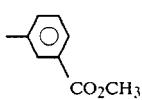 | methyl | 110 |
| 65 | 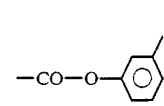 | phenyl | methyl | 121 |
| 66 | 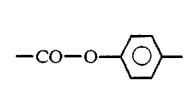 | phenyl | methyl | 145–147 |
| 67 | acetyl | 3-methylphenyl | methyl | 55–58 |
| 68 | 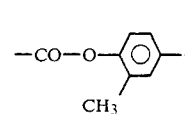 | 3-Cl-phenyl | methyl | 136–139 |
| 69 | 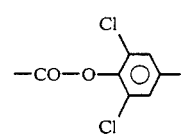 | 3-Cl-phenyl | methyl | 111–113 |

Application of the herbicides may be effected for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the above ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 1 to 90, % by weight of active ingredient. Application rates are from 0.1 to 15 kg and more of active ingredient per hectare, but are preferably from 0.2 to 3.0 kg/ha.

The 3-aryl-5-methylpyrazole-4-carboxylic acid esters according to the invention may be mixed with each other or mixed and applied together with numerous representatives of other herbicidal or growth-regulating active ingredient groups. Examples of suitable mixture components are diazines, benzothiadiazinones, 2,6-dinitroanilines, N-phenylcarbamates, biscarbamates, thiolcarbamates, halocarboxylic acids, triazines, amides, ureas, diphenyl ethers, triazinones, uracils, benzofuran derivatives, etc. Such combinations broaden the spectrum of action, and sometimes synergistic effects are achieved.

As the herbicides are predominantly postemergence agents, they are excellently supplemented by components which preferably act through the soil. A number of active ingredients which, when combined with the new compounds, give mixtures useful for widely varying applications are given below by way of example:
5-amino-4-chloro-2-phenyl-3(2H)-pyridazinone
5-amino-4-bromo-2-phenyl-3(2H)-pyridazinone
5-amino-4-chloro-2-cyclohexyl-3(2H)-pyridazinone
5-amino-4-bromo-2-cyclohexyl-3(2H)-pyridazinone
5-methylamino-4-chloro-2-(3-trifluoromethylphenyl)-3(2H)-pyridazinone 5-methylamino-4-chloro-2-(3-,α,α,β,β-tetrafluoroethoxyphenyl)-3(2H)-pyridazinone
5-dimethylamino-4-chloro-2-phenyl-3(2H)-pyridazinone 4,5-dimethoxy-2-phenyl-3(2H)-pyridazinone
4,5-dimethoxy-2-cyclohexyl-3(2H)-pyridazinone
4,5-dimethoxy-2-(3-trifluoromethylphenyl)-3(2H)-pyridazinone
5-methoxy-4-chloro-2-(3-trifluoromethylphenyl)-3(2H)-pyridazinone
5-amino-4-bromo-2-(3-methylphenyl)-3(2H)-pyridazinone
3-(1-methylethyl)-1H-2,1,3-benzothiadiazin-4(3H)-one-2,2-dioxide and salts
3-(1-methylethyl)-8-chloro-1H-2,1,3-benzothiadiazin-4(3H)-one-2,2-dioxide and salts
3-(1-methylethyl)-8-fluoro-1H-2,1,3-benzothiadiazin-4(3H)-one-2,2-dioxide and salts
3-(1-methylethyl)-8-methyl-1H-2,1,3-benzothiadiazin-4(3H)-one-2,2-dioxide and salts
1-methoxymethyl-3-(1-methylethyl)-2,1,3-benzothiadiazin-4(3H)-one-2,2-dioxide
1-methoxymethyl-8-chloro-3-(1-methylethyl)-2,1,3-benzothiadiazin-4(3H)-one-2,2-dioxide
1-methoxymethyl-8-fluoro-3-(1-methylethyl)-2,1,3-benzothiadiazin-4(3H)-one-2,2-dioxide
1-cyano-8-chloro-3-(1-methylethyl)-2,1,3-benzothiadiazin-4(3H)-one-2,2-dioxide
1-cyano-8-fluoro-3-(1-methylethyl)-2,1,3-benzothiadiazin-4(3H)-one-2,2-dioxide
1-cyano-8-methyl-3-(1-methylethyl)-2,1,3-benzothiadiazin-4(3H)-one-2,2-dioxide
1-cyano-3-(1-methylethyl)-2,1,3-benzothiadiazin-4(3H)-one-2,2-dioxide
1-azidomethyl-3-(1-methylethyl)-2,1,3-benzothiadiazin-4(3H)-one-2,2-dioxide
3-(1-methylethyl)-1H-pyridino-[3,2-e]-2,1,3-thiadiazin-(4)-one-2,2-dioxide
N-(1-ethylpropyl)-2,6-dinitro-3,4-dimethylaniline
N-(1-methylethyl)-N-ethyl-2,6-dinitro-4-trifluoromethylaniline
N-n-propyl-N-β-chloroethyl-2,6-dinitro-4-trifluoromethylaniline
N-n-propyl-N-cyclopropylmethyl-2,6-dinitro-4-trifluoromethylaniline
N-bis-(n-propyl)-2,6-dinitro-3-amino-4-trifluoromethylaniline
N-bis-(n-propyl)-2,6-dinitro-4-methylaniline
N-bis-(n-propyl)-2,6-dinitro-4-methylsulfonylaniline
N-bis-(n-propyl)-2,6-dinitro-4-aminosulfonylaniline
bis-(β-chloroethyl)-2,6-dinitro-4-methylaniline
N-ethyl-N-(2-methylallyl)-2,6-dinitro-4-trifluoromethylaniline
3,4-dichlorobenzyl N-methylcarbamate
2,6-di-tert.butyl-4-methylphenyl N-methylcarbamate
isopropyl N-phenylcarbamate
3-methoxyprop-2-yl N-3-fluorophenylcarbamate
isopropyl N-3-chlorophenylcarbamate
but-1-yn-3-yl N-3-chlorophenylcarbamate
4-chlorobut-2-yn-1-yl N-3-chlorophenylcarbamate
methyl N-3,4-dichlorophenylcarbamate
methyl N-(4-aminobenzenesulfonyl)-carbamate
O-(N-phenylcarbamoyl)-propanonoxime
N-ethyl-2-(phenylcarbamoyl)-oxypropionic acid amide
3'-N-isopropylcarbamoyloxypropionanilide
ethyl-N-(3-(N'-phenylcarbamoyloxy)-phenyl)-carbamate
methyl-N-(3-(N'-methyl-N'-phenylcarbamoyloxy)-phenyl)-carbamate
isopropyl-N-(3-(N'-ethyl-N'-phenylcarbamoyloxy)-phenyl)-carbamate
methyl-N-(3-(N'-3-methylphenylcarbamoyloxy)-phenyl)-carbamate
methyl-N-(3-(N'-4-fluorophenylcarbamoyloxy)-phenyl)-carbamate
methyl-N-(3-(N'-3-chloro-4-fluorophenylcarbamoyloxy)-phenyl)-carbamate
ethyl-N-[3-N'-(3-chloro-4-fluorophenylcarbamoyloxy)-phenyl]-carbamate
ethyl-N-[3-N'-(3,4-difluorophenylcarbamoyloxy)-phenyl]-carbamate
methyl-N-[3-(N'-3,4-difluorophenylcarbamoyloxy)-phenyl]-carbamate
methyl N-3-(4'-fluorophenoxycarbonylamino)-phenyl-carbamate
ethyl N-3-(2'-methylphenoxycarbonylamino)-phenyl-carbamate
methyl N-3-(4'-fluorophenoxycarbonylamino)-phenyl-thiolcarbamate
methyl N-3-(2',4',5'-trimethylphenoxycarbonylamino)-phenylthiolcarbamate
methyl N-3-(phenoxycarbonylamino)-phenylthiolcarbamate
p-chlorobenzyl N,N-diethylthiolcarbamate
ethyl N,N-di-n-propylthiolcarbamate
n-propyl N,N-di-n-propylthiolcarbamate
2,3-dichloroallyl N,N-diisopropylthiolcarbamate
2,3,3-trichloroalkyl N,N-diisopropylthiolcarbamate
3-methyl-5-isoxazolylmethyl N,N-diisopropylthiolcarbamate
3-ethyl-5-isoxazolylmethyl N,N-diisopropylthiolcarbamate
ethyl N,N-di-sec.-butylthiolcarbamate
benzyl N,N-di-sec.-butylthiolcarbamate
ethyl N-ethyl-N-cyclohexylthiolcarbamate
ethyl N-ethyl-N-bicyclo-[2.1.1]-heptylthiolcarbamate
S-(2,3-dichloroallyl)-(2,2,4-trimethylazetidine)-1-carbothiolate
S-(2,3,3-trichloroallyl)-(2,2,4-trimethylazetidine)-1-carbothiolate
S-ethylhexahydro-1-H-azepine-1-carbothiolate
S-benzyl-(3-methylhexahydro-1-H-azepine-1)-carbothiolate
S-benzyl-(2,3-dimethylhexahydro-1-H-azepine-1)-carbothiolate
S-ethyl-(3-methylhexahydro-1-H-azepine-1)-carbothiolate
n-propyl N-ethyl-N-n-butylthiolcarbamate
2-chloroallyl N,N-dimethyldithiocarbamate
N-methyldithiocarbamic acid, sodium salt
trichloroacetic acid, sodium salt
α,α-dichloropropionic acid, sodium salt
α,α-dichlorobutyric acid, sodium salt
α,α-β,β-tetrafluoropropionic acid, sodium salt
α-methyl-α,β-dichloropropionic acid, sodium salt
methyl α-chloro-β-(4-chlorophenyl)-propionate
methyl α,β-dichloro-β-phenylpropionate
benzamido oxyacetic acid
2,3,5-triiodobenzoic acid (salts, esters, amides)
2,3,6-trichlorobenzoic acid (salts, esters, amides)
2,3,5,6-tetrachlorobenzoic acid (salts, esters, amides)
2-methoxy-3,6-dichlorobenzoic acid (salts, esters, amides)
2-methoxy-3,5,6-trichlorobenzoic acid (salts, esters, amides)
3-amino-2,5,6-trichlorobenzoic acid (salts, esters, amides)

O,S-dimethyltetrachlorothioterephthalate
dimethyl-2,3,5,6-tetrachloroterephthalate
disodium-3,6-endooxohexahydrophthalate
4-amino-3,5,6-trichloropicolinic acid (salts)
ethyl 2-cyano-3-(N-methyl-N-phenyl)-aminoacrylate
isobutyl 2-[4-(4'-chlorophenoxy)-phenoxy]-propionate
methyl 2-[4-(2',4'-dichlorophenoxy)-phenoxy]-propionate
methyl 2-[4-(4'-trifluoromethylphenoxy)-phenoxy]-propionate
2-[4-(2'-chloro-4'-trifluorophenoxy)-phenoxy]-propionic acid, sodium salt
2-[4-(3',5'-dichloropyridyl-2-oxy)-phenoxy]-propionic acid, sodium salt
ethyl 2-(N-benzoyl-3,4-dichlorophenylamino)-propionate
methyl 2-(N-benzoyl-3-chloro-4-fluorophenylamino)-propionate
isopropyl 2-(N-benzoyl-3-chloro-4-fluorophenylamino)-propionate
2-chloro-4-ethylamino-6-isopropylamino-1,3,5-triazine
2-chloro-4-ethylamino-6-(amino-2'-propionitrile)-1,3,5-triazine
2-chloro-4-ethylamino-6-(2-methoxypropyl)-2-amino-1,3,5-triazine
2-chloro-4-ethylamino-6-butyn-1-yl-2-amino-1,3,5-triazine
2-chloro-4,6-bisethylamino-1,3,5-triazine
2-chloro-4,6-bisisopropylamino-1,3,5-triazine
2-chloro-4-isopropylamino-6-cyclopropylamino-1,3,5-triazine
2-azido-4-methylamino-6-isopropylamino-1,3,5-triazine
2-methylthio-4-ethylamino-6-isopropylamino-1,3,5-triazine
2-methylthio-4-ethylamino-6-tert.butylamino-1,3,5-triazine
2-methylthio-4,6-bisethylamino-1,3,5-triazine
2-methylthio-4,6-bisisopropylamino-1,3,5-triazine
2-methoxy-4-ethylamino-6-isopropylamino-1,3,5-triazine
2-methoxy-4,6-bisethylamino-1,3,5-triazine
2-methoxy-4,6-bisisopropylamino-1,3,5-triazine
4-amino-6-tert.butyl-3-methylthio-4,5-dihydro-1,2,4-triazin-5-one
4-amino-6-phenyl-3-methyl-4,5-dihydro-1,2,4-triazin-5-one
4-isobutylidenamino-6-tert.butyl-3-methylthio-4,5-dihydro-1,2,4-triazin-5-one
1-methyl-3-cyclohexyl-6-dimethylamino-1,3,5-triazine-2,4-dione
3-tert.butyl-5-chloro-6-methyluracil
3-tert.butyl-5-bromo-6-methyluracil
3-isopropyl-5-bromo-6-methyluracil
3-sec.butyl-5-bromo-6-methyluracil
3-(2-tetrahydropyranyl)-5-chloro-6-methyluracil
3-(2-tetrahydropyranyl)-5,6-trimethyleneuracil
3-cyclohexyl-5,6-trimethyleneuracil
2-methyl-4-(3'-trifluoromethylphenyl)-tetrahydro-1,2,4-oxadiazine-3,5-dione
2-methyl-4-(4'-fluorophenyl)-tetrahydro-1,2,4-oxadiazine-3,5-dione 3-amino-1,2,4-triazole
1-allyloxy-1-(4-bromophenyl)-2-[1',2',4'-triazolyl-(1')]-ethane (salts)
1-(4-chlorophenoxy)-3,3-dimethyl-1-(1H-1,2,3-triazol-1-yl)-butan-2-one
N,N-diallylchloroacetamide
N-isopropyl-2-chloroacetanilide
N-(but-1-yn-3-yl)-2-chloroacetanilide
2-methyl-6-ethyl-N-propargyl-2-chloroacetanilide
2-methyl-6-ethyl-N-ethoxymethyl-2-chloroacetanilide
2-methyl-6-ethyl-N-(2-methoxy-1-methylethyl)-2-chloroacetanilide
2-methyl-6-ethyl-N-(isopropoxycarbonylethyl)-2-chloroacetanilide
2-methyl-6-ethyl-N-(4-methoxypyrazol-1-yl-methyl)-2-chloroacetanilide
2-methyl-6-ethyl-N-(pyrazol-1-yl-methyl)-2-chloroacetanilide
2,6-dimethyl-N-(pyrazol-1-yl-methyl)-2-chloroacetanilide
2,6-dimethyl-N-(4-methylpyrazol-1-yl-methyl)-2-chloroacetanilide
2,6-dimethyl-N-(1,2,4-triazol-1-yl-methyl)-2-chloroacetanilide
2,6-dimethyl-N-(3,5-dimethylpyrazol-1-yl-methyl)-2-chloroacetanilide
2,6-dimethyl-N-(1,3-dioxolan-2-yl-methyl)-2-chloroacetanilide
2,6-dimethyl-N-(2-methoxyethyl)-2-chloroacetanilide
2,6-dimethyl-n-isobutoxymethyl-2-chloroacetanilide
2,6-diethyl-n-methoxymethyl-2-chloroacetanilide
2,6-diethyl-N-n-butoxymethyl-2-chloroacetanilide
2,6-diethyl-N-ethoxycarbonylmethyl-2-chloroacetanilide
2,3,6-trimethyl-N-(pyrazol-1-yl-methyl)-2-chloroacetanilide
2,3-dimethyl-N-isopropyl-2-chloroacetanilide
2,6-dimethyl-N-(propoxyethyl)-2-chloroacetanilide
2-(2-methyl-4-chlorophenoxy-N-methoxyacetamide
2-(α-naphthoxy)-N,N-diethylpropionamide
2,2-diphenyl-N,N-dimethylacetamide
α-(3,4,5-tribromopyrazol-1-yl)-N,N-dimethylpropionamide
N-(1,1-dimethylpropynyl)-3,5-dichlorobenzamide
N-1-naphthylphthalamic acid
propionic acid-3,4-dichloroanilide
cyclopropanecarboxylic acid-3,4-dichloroanilide
methacrylic acid-3,4-dichloroanilide
2-methylpentanecarboxylic acid-3,4-dichloroanilide
N-2,4-dimethyl-5-(trifluoromethyl)-sulfonylamino-phenylacetamide
N-4-methyl-5-(trifluoromethyl)-sulfonylamino-phenylacetamide
2-propionylamino-4-methyl-5-chlorothiazole
O-(methylsulfonyl)-glycolic acid-N-ethoxymethyl-2,6-dimethylanilide
O-(methylaminosulfonyl)-glycolic acid-N-isopropylanilide
O-(isopropylaminosulfonyl)-glycolic acid-N-but-1-yn-3-yl-anilide
O-(methylaminosulfonyl)-glycolic acid hexamethyleneamide
2,6-dichlorothiobenzamide
2,6-dichlorobenzonitrile
3,5-dibromo-4-hydroxybenzonitrile (salts)
3,5-diiodo-4-hydroxybenzonitrile (salts)
3,5-dibromo-4-hydroxy-O-2.4-dinitrophenylbenzaldoxime (salts)
3,5-dibromo-4-hydroxy-O-2-cyano-4-nitrophenylbenzaldoxime (salts)
pentachlorophenol, sodium salt
2,4-dichlorophenyl-4'-nitrophenyl ether
2,4,6-trichlorophenyl-4'-nitrophenyl ether
2-fluoro-4,6-dichlorophenyl-4'-nitrophenyl ether
2-chloro-4-trifluoromethylphenyl-4'-nitrophenyl ether
2,4'-dinitro-4-trifluoromethyl-diphenyl ether 2,4-dichlorophenyl-3'-methoxy-4'-nitro-phenyl ether
2-chloro-4-trifluoromethylphenyl-3'-ethoxy-4'-nitro-phenyl ether
2-chloro-4-trifluoromethylphenyl-3'-carboxy-4'-nitro-phenyl ether (salts)
2,4-dichlorophenyl-3'-methoxycarbonyl-4'-nitro-phenyl ether
2-(3,4-dichlorophenyl)-4-methyl-1,2,4-oxadiazolidine-3,5-dione
2-(3-tert.butylcarbamoyloxyphenyl)-4-methyl-1,2,4-oxadiazolidine-3,5-dione
2-(3-isopropylcarbamoyloxyphenyl)-4-methyl-1,2,4-oxadiazolidine-3,5-dione
2-phenyl-3,1-benzoxazinone-(4)
(4-bromophenyl)-3,4,5,9,10-pentaazatetracyclo-[5,4,1,0$^{2,6}$,O,$^{8,11}$]-dodeca-3,9-diene
2-ethoxy-2,3-dihydro-3,3-dimethyl-5-benzofuranylmethane sulfonate
2-ethoxy-2,3-dihydro-3,3-dimethyl-5-benzofuranyl-dimethylaminosulfate
2-ethoxy-2,3-dihydro-3,3-dimethyl-5-benzofuranyl-(N-methyl-N-acetyl)-aminosulfonate
3,4-dichloro-1,2-benzisothiazole
N-4-chlorophenyl-allylsuccinimide
2-methyl-4,6-dinitrophenol (salts, esters)
2-sec.butyl-4,6-dinitrophenol (salts, esters)
2-sec.butyl-4,6-dinitrophenol acetate
2-tert.butyl-4,6-dinitrophenol acetate
2-tert.butyl-4,6-dinitrophenol (salts)
2-tert.butyl-5-methyl-4,6-dinitrophenol (salts)
2-tert.butyl-5-methyl-4,6-dinitrophenol acetate
2-sec.amyl-4,6-dinitrophenol (salts, esters)
1-(α,α-dimethylbenzyl)-3-(4-methylphenyl)-urea
1-phenyl-3-(2-methylcyclohexyl)-urea
1-phenyl-1-benzoyl-3,3-dimethylurea
1-(4-chlorophenyl)-1-benzoyl-3,3-dimethylurea
1-(4-chlorophenyl)-3,3-dimethylurea
1-(4-chlorophenyl)-3-methyl-3-but-1-yn-3-yl-urea
1-(3,4-dichlorophenyl)-3,3-dimethylurea
1-(3,4-dichlorophenyl)-1-benzoyl-3,3-dimethylurea
1-(3,4-dichlorophenyl)-3-methyl-3-n.butylurea
1-(4-isopropylphenyl)-3,3-dimethylurea
1-(3-trifluoromethylphenyl)-3,3-dimethylurea
1-(α,α,β,β-tetrafluoroethoxyphenyl)-3,3-dimethylurea
1-(3-tert.butylcarbamoyloxyphenyl)-3,3-dimethylurea
1-(3-chloro-4-methylphenyl)-3,3-dimethylurea
1-(3-chloro-4-methoxyphenyl)-3,3-dimethylurea
1-(3,5-dichloro-4-methoxyphenyl)-3,3-dimethylurea
1-[4-(4'-chlorophenoxy)-phenyl]-3,3-dimethylurea
1-[4-(4'-methoxyphenoxy)-phenyl]-3,3-dimethylurea
1-cyclooctyl-3,3-dimethylurea
1-(hexahydro-4,7-methanoindan-5-yl)-3,3-dimethylurea
1-[1- or 2-(3a,4,5,7,7a-hexahydro)-4,7-methanoindanyl]-3,3-dimethylurea
1-(4-fluorophenyl)-3-carboxymethoxy-3-methylurea
1-phenyl-3-methyl-3-methoxyurea
1-(4-chlorophenyl)-3-methyl-3-methoxyurea
1-(4-bromophenyl)-3-methyl-3-methoxyurea
1-(3,4-dichlorophenyl)-3-methyl-3-methoxyurea
1-(3-chloro-4-bromophenyl)-3-methyl-3-methoxyurea
1-(3-chloro-4-isopropylphenyl)-3-methyl-3-methoxyurea
1-(3-chloro-4-methoxyphenyl)-3-methyl-3-methoxyurea
1-(3-tert.butylphenyl)-3-methyl-3-methoxyurea
1-(2-benzthiazolyl)-1,3-dimethylurea
1-(2-benzthiazolyl)-3-methylurea
1-(5-trifluoromethyl-1,3,4-thiadiazolyl)-1,3-dimethylurea
imidazolidin-2-one-1-carboxylic acid isobutylamide
1,2-dimethyl-3,5-diphenylpyrazolium-methylsulfate
1,2,4-trimethyl-3,5-diphenylpyrazolium-methylsulfate
1,2-dimethyl-4-bromo-3,5-diphenylpyrazolium-methylsulfate
1,3-dimethyl-4-(3,4-dichlorobenzoyl)-5-(4-methylphenylsulfonyloxy)-pyrazole
2,3,5-trichloropyridinol-(4)
1-methyl-3-phenyl-5-(3'-trifluoromethylphenyl)-pyridone-(4)
1-methyl-4-phenylpyridinium chloride
1,1-dimethylpyridinium chloride
3-phenyl-4-hydroxy-6-chloropyridazine
1,1'-dimethyl-4,4'-dipyridylium-di(methylsulfate)
1,1'-di-(3,4-dimethylmorpholine-carbonylmethyl)-4,4'-dipyridylium dichloride
1,1'-ethylene-2,2'-dipyridylium dibromide
3-[1-(N-ethoxyamino)-propylidene]-6-ethyl-3,4-dihydro-2H-pyran-2,4-dione
3-[1-(N-allyloxyamino)-propylidene]-6-ethyl-3,4-dihydro-2H-pyran-2,4-dione
2-[1-(N-allyloxyamino)-propylidene]-5,5-dimethylcyclohexane-1,3-dione (salts)
2-[1-(N-allyloxyamino-butylidene]-5,5-dimethylcyclohexane-1,3-dione (salts)
2-[1-(N-allyloxyamino-butylidene]-5,5-dimethyl-4-methoxycarbonyl-cyclohexane-1,3-dione (salts)
2-chlorophenoxyacetic acid (salts, esters, amides)
4-chlorophenoxyacetic acid (salts, esters, amides)
2,4-dichlorophenoxyacetic acid (salts, esters, amides)
2,4,5-trichlorophenoxyacetic acid (salts, esters, amides)
2-methyl-4-chlorophenoxyacetic acid (salts, esters, amides)
3,5,6-trichloro-2-pyridinyl-oxyacetic acid (salts, esters, amides)
methyl α-naphthoxyacetate
2-(2-methylphenoxy)-propionic acid (salts, esters, amides)
2-(4-chlorophenoxy)-propionic acid (salts, esters, amides)
2-(2,4-dichlorophenoxy)-propionic acid (salts, esters, amides)
2-(2,4,5-trichlorophenoxy)-propionic acid (salts, esters, amides)
2-(2-methyl-4-chlorophenoxy)-propionic acid (salts, esters, amides)
4-(2,4-dichlorophenoxy)-butyric acid (salts, esters, amides)
4-(2-methyl-4-chlorophenoxy)-butyric acid (salts, esters, amides)
cyclohexyl-3-(2,4-dichlorophenoxy)-acrylate
9-hydroxyfluorenecarboxylic acid-(9) (salts, esters)
2,3,6-trichlorophenylacetic acid (salts, esters)
4-chloro-2-oxobenzothiazolin-3-yl-acetic acid (salts, esters)
gibelleric acid (salts)
disodium methylarsonate
monosodium salt of methylarsonic acid
N-phosphonomethyl-glycine (salts)
N,N-bis-(phosphonomethyl)-glycine (salts)
2-chloroethyl 2-chloroethanephosphonate
ammonium-ethyl-carbamoyl-phosphonate
di-n-butyl-1-n-butylamino-cyclohexyl-phosphonate
trithiobutylphosphite
O,O-diisopropyl-5-(2-benzosulfonylaminoethyl)-phosphorodithionate 2,3-dihydro-5,6-dimethyl-1,4-dithiin-1,1,4,4-tetraoxide
5-tert.butyl-3-(2,4-dichloro-5-isopropoxyphenyl)-1,3,4-oxadiazolone-(2)
4,5-dichloro-2-trifluoromethylbenzimidazole (salts)
1,2,3,6-tetrahydropyridazine-3,6-dione (salts)
succinic acid mono-N-dimethylhydrazide (salts)
(2-chloroethyl)-trimethylammonium chloride
(2-methyl-4-phenylsulfonyl)-trifluoromethanesulfone anilide
1,1-dimethyl-4,6-diisopropyl-5-indanyl ethyl ketone
sodium chlorate
ammonium thiocyanate
calcium cyanamide
2-chloro-4-trifluoromethyl-3'-ethoxycarbonyl-4'-nitrophenyl ether
1-(4-benzyloxyphenyl)-3-methyl-3-methoxyurea
2-[1-(2,5-dimethylphenyl)-ethylsulfonyl]-pyridine-N-oxide.

It may also be useful to apply the active ingredients, either alone or in combination with other herbicides, in admixture with other crop protection agents, e.g., agents for combating pests or phytopathogenic fungi or bacteria. The compounds may also be mixed with solutions of mineral matters used to remedy nutritional or trace element deficiencies. To initiate the herbicidal action, wetting agents, spreader-stickers and non-phytotoxic oils and oil concentrates may be added.

The following greenhouse experiments demonstrate the influence of various herbicides on the growth of crop and unwanted plants.

The vessels employed were plastic flowerpots having a volume of 300 cm³, and which were filled with a sandy loam containing about 1.5% humus. The seeds of the test plants (cf. Table 1) were sown shallow, and separately, according to species. For the postemergence treatment, the plants were grown to a height of from 3 to 10 cm. Certain test plant species were first grown as seedlings in special seedling vessels before being transplanted to the plastic pots described above. The chemical agents were then applied a few days after the plants had taken root. The active ingredients were suspended or emulsified in water as vehicle and sprayed onto the plants through finely distributing nozzles. The pots were then set up in the greenhouse—species from warmer areas at from 25° to 40° C., and species from moderate climates at from 15° to 30° C. The experiments were run for from 3 to 6 weeks. During this period, the plants were tended and their reactions to the various treatments assessed. The following tables containing the compounds investigated, the application rates in kg/ha of active ingredient, and the plants used for the tests. The scale used for assessment was 0 to 100, 0 denoting no damage or normal emergence, and 100 denoting nonemergence or complete destruction of at least the visible plant parts.

The selective herbicidal action of the active ingredients is demonstrated in the following tables. The compounds are predominantly applied postemergence, but they also have an effect when applied preemergence. A special application technique consists in spraying the active ingredients with spray equipment in such a manner that the leaves of sensitive crop plants are if possible not contacted, and the active ingredients reach the soil or the unwanted plants growing there (post-directed, lay-by). In addition to the unwanted plants listed in the tables, the wild oat species Avena fatua and Avena ludoviciana, slender foxtail (Alopecurus myosuroides) and numerous other unwanted grasses and weeds are combated.

In view of the wide variety of application methods, the herbicides, or mixtures containing them, may be used to combat unwanted plant growth in a large number of crops.

The following crop plants may be mentioned as examples:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rape |
| Brassica napus var. napobrassica | |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |

-continued

| Botanical name | Common name |
|---|---|
| Ribes uva-crispa | |
| Ricinus communis | |
| Saccharum officinarum | sugar cane |
| Secale cereale | rye |
| Sesamum indicum | sesame |
| Solanum tuberosum | Irish potatoes |
| Sorghum bicolor (s. vulgare) | grain sorghum |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

TABLE 1

List of plants used in the experiments

| Botanical name | Abbreviation in tables | Common name |
|---|---|---|
| Amaranthus retroflexus | Amar. retr. | redroot pigweed |
| Arachis hypogaea | Arachis hyp. | peanuts (ground nuts) |
| Datura stramonium | Datura stram. | jimsonweed |
| Echinochloa crus galli | Echinochl. c.g. | barnyardgrass |
| Hordeum vulgare | Hordeum vulg. | barley |
| Ipomoea spp. | | morningglory |
| Lamium amplexicaule | Lamium amplexic. | henbit |
| Nicandra physaloides | Nicandra phys. | apple-of-Peru |
| Rumex optusifolius | Rumex otus. | broadleaf dock |
| Sesbania exaltata | Sesbania exalt. | hemp sesbania (coffee weed) |
| Sorghum bicolor | | sorghum |
| Sorghum halepense | Sorghum halep. | Johnsongrass |
| Sinapis alba | | white mustard |
| Triticum aestivum | Tritic. aest. | wheat |
| Solanum nigrum | | black nightshade |

TABLE 2

Selective control of broadleaved weeds in wheat; postemergence application in the greenhouse

| Compound no. | kg/ha | Tritic. aest. | Lamium amplexic. | Sinapis alba | Solanum nigrum |
|---|---|---|---|---|---|
| 5 | 0.5 | 10 | 80 | 95 | 100 |
| 22 | 0.25 | 0 | 100 | 95 | 100 |
| 28 | 0.5 | 0 | 90 | — | — |
| 6 | 0.25 | 0 | 100 | 95 | 100 |
| 8 | 0.25 | 10 | 100 | 95 | 100 |
| 12 | 0.25 | 10 | 100 | 90 | 100 |
| 7 | 0.25 | 0 | 100 | 90 | 100 |
| 9 | 0.25 | 10 | 100 | 90 | 100 |
| 16 | 0.25 | 10 | 100 | 90 | — |
| 18 | 0.5 | 0 | 100 | 85 | 100 |
| 42 | 0.25 | 0 | 100 | 95 | 100 |
| 35 | 1.0 | 0 | 100 | 95 | 100 |
| 38 | 0.5 | 0 | 100 | 90 | 100 |
| 39 | 0.25 | 10 | 100 | 95 | 100 |
| 40 | 0.25 | 0 | — | 90 | 100 |
| 46 | 0.25 | 0 | 100 | 95 | 100 |
| 41 | 0.25 | 0 | 100 | 95 | 100 |
| 47 | 0.25 | 0 | 100 | 90 | 100 |
| 48 | 1.0 | 10 | 100 | — | 100 |
| (U.S. Pat. No. 4,116,673) | 2.0 | 10 | 20 | 20 | 40 |

A = 1-methyl-3-[3'-trifluoromethylphenyl]-4-methoxycarbonyl-pyrazole

| (U.S. Pat. No. 4,116,673) | 2.0 | 0 | 40 | 20 | 30 |

B = 1-methyl-3-phenyl-4-ethoxycarbonylpyrazole

0 = no damage
100 = plants destroyed

TABLE 3

Control of unwanted broadleaved plants in sorghum; postemergence treatment in the greenhouse

| Compound no. | kg/ha | Sorghum bicolor | Amar. retr. | Datura stram. | Nicandra phys. | Sesbania exalt. |
|---|---|---|---|---|---|---|
| 6 | 0.25 | 10 | 80 | 98 | 100 | 100 |
| 14 | 1.0 | 10 | 100 | 100 | 100 | 100 |
| 33 | 1.0 | 5 | 70 | 100 | 100 | 100 |
| 34 | 2.0 | 10 | 100 | 100 | 100 | 100 |
| 8 | 0.5 | 0 | 100 | 100 | 100 | 98 |
| 41 | 0.5 | 0 | 100 | 100 | 100 | 100 |
| 47 | 1.0 | 5 | 100 | 100 | 100 | 100 |
| 1 | 0.5 | 5 | 70 | 100 | 100 | 100 |
| 7 | 0.5 | 0 | — | 98 | 100 | 100 |
| 42 | 0.5 | 10 | 100 | 100 | 100 | 100 |
| 40 | 1.0 | 10 | 100 | 100 | 100 | 100 |
| 46 | 1.0 | 10 | 100 | 100 | 100 | 100 |
| A | 2.0 | 5 | 0 | 10 | 20 | 90 |
| B | 2.0 | 15 | 0 | 30 | 40 | 10 |

0 = no damage
100 = plants destroyed

TABLE 4

Control of unwanted plant growth in groundnuts; postemergence treatment in the greenhouse

| Compound no. | kg/ha | Arachis hyp. | Amar. retr. | Echinochl. c.g. | Ipomoea spp. | Sorghum halep. |
|---|---|---|---|---|---|---|
| 31 | 2.0 | 5 | 100 | 100 | 95 | 85 |
| 10 | 1.0 | 10 | 100 | 95 | 95 | 95 |
| 25 | 1.0 | 10 | 100 | 90 | 80 | 90 |
| 36 | 2.0 | 10 | 60 | 94 | 100 | 88 |
| 9 | 1.0 | 0 | 45 | 90 | 80 | 95 |
| 39 | 1.0 | 0 | 100 | 95 | 100 | 85 |
| 41 | 1.0 | 5 | 100 | 98 | 100 | 90 |
| 47 | 1.0 | 5 | 100 | 80 | 90 | 85 |
| 6 | 2.0 | 0 | 100 | 98 | 100 | 80 |
| 16 | 2.0 | 0 | 60 | 100 | 60 | 100 |
| 42 | 2.0 | 0 | 100 | 90 | 70 | 98 |
| A | 2.0 | 0 | 0 | 0 | 0 | 0 |
| (U.S. Pat. No. 4,116,673) | | | | | | |
| C | 2.0 | 0 | 0 | 0 | 0 | 0 |

C = 1-methyl-3-[3'-trifluoromethylphenyl]-4-ethoxycarbonyl-pyrazole

0 = no damage
100 = plants destroyed

TABLE 5

Herbicidal action on Ipomoea spp.; postemerrgence treatment in the greenhouse

| Compound no. | kg/ha | Damage (%) to Ipomoea spp. |
|---|---|---|
| 15 | 3.0 | 100 |
| 24 | 3.0 | 100 |
| 32 | 3.0 | 100 |
| 37 | 3.0 | 100 |
| 43 | 3.0 | 100 |
| 44 | 3.0 | 100 |
| 45 | 3.0 | 100 |
| 26 | 3.0 | 90 |
| 29 | 3.0 | 100 |
| 52 | 3.0 | 100 |
| 54 | 3.0 | 100 |
| 55 | 3.0 | 100 |

TABLE 6

Selective control of unwanted plants in cereals; postemergence treatment in the greenhouse

| Compound no. | kg/ha | Hordeum vulg. | Tritic. aest. | Lamium amplex. | Rumex obtus. | Sinapis alba |
|---|---|---|---|---|---|---|
| 2 | 0.5 | 0 | 0 | 80 | 90 | 95 |
| B | 0.5 | 0 | 0 | 30 | 0 | 10 |

EXAMPLE 1

90 parts by weight of compound 1 is mixed with 10 parts by weight of N-methyl-α-pyrrolidone. A mixture is obtained which is suitable for application in the form of very fine drops.

EXAMPLE 2

20 parts by weight of compound 2 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE 3

20 parts by weight of compound 3 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

EXAMPLE 4

20 parts by weight of compound 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE 5

20 parts by weight of compound 3 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

EXAMPLE 6

3 parts by weight of compound 3 is intimately mixed with 97 parts by weight of particulate kaolin. A dust is obtained containing 3% by weight of the active ingredient.

EXAMPLE 7

30 parts by weight of compound 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 8

40 parts by weight of compound 1 is intimately mixed with 10 parts of the sodium salt of a phenolsulfonic acid-urea-formaldehyde condensate, 2 parts of silica gel and 48 parts of water. Dilution in 100,000 parts by weight of water gives an aqueous dispersion containing 0.04 wt% of active ingredient.

EXAMPLE 9

20 parts of compound 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:

1. A process for combating the growth of unwanted plants, wherein the plants are treated with a herbicidally effective amount of a pyrazole derivative of the formula

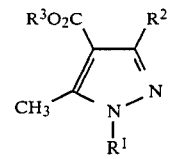

where $R^1$ denotes hydrogen, $R^2$ denotes phenyl which is unsubstituted or mono-substituted by fluorine, chlorine, bormine, methyl methoxy, cyano trifluoromethyl, trifluoromethoxy or methoxycarbonyl, $R^2$ further denotes, an unsubstituted or methyl- or chloro-substituted thienyl, furyl, oxazolyl or pyridyl, or $R^2$ denotes α-naphthyl or β-naphthyl, and $R^3$ denotes methyl, or a salt thereof.

* * * * *